United States Patent [19]

Schwabe et al.

[11] Patent Number: 5,548,002
[45] Date of Patent: Aug. 20, 1996

[54] PROVISIONAL LUTING MATERIALS

[75] Inventors: Peter Schwabe, Leverkusen; Ottfried Schlak; Jens Winkel, both of Cologne; Rainer Guggenberger, Herrsching; Oswald Gasser, Seefeld, all of Germany

[73] Assignee: Heraeus Kulzer GmbH & Co. KG, Hanau, Germany

[21] Appl. No.: 404,710

[22] Filed: Mar. 15, 1995

Related U.S. Application Data

[62] Division of Ser. No. 858,912, Mar. 27, 1992, abandoned.

[51] Int. Cl.$^6$ .............. A61C 13/23; C08L 83/02; C08K 5/56
[52] U.S. Cl. .............. 523/118; 523/115; 523/116; 524/730; 524/859; 528/17; 528/18; 433/228.1; 106/287.16
[58] Field of Search .................. 523/115, 116, 523/118; 528/17, 18; 524/730, 859; 433/228.1; 106/287.16

[56] References Cited

U.S. PATENT DOCUMENTS

| | | | |
|---|---|---|---|
| 3,082,527 | 3/1963 | Nitzsche et al. | 528/18 |
| 3,186,963 | 6/1965 | Lewis et al. | 528/18 |
| 3,258,382 | 6/1966 | Vincent | 528/17 |
| 3,574,943 | 3/1969 | Stark et al. | |
| 3,664,997 | 5/1972 | Chadha et al. | 528/18 |
| 3,957,704 | 5/1976 | Smith et al. | 528/17 |
| 4,267,297 | 5/1981 | Hanada et al. | 528/18 |
| 4,273,834 | 6/1981 | Yokokura et al. | 528/17 |
| 4,408,031 | 10/1983 | Holtschmidt et al. | 528/17 |
| 4,486,476 | 12/1984 | Fritsch et al. | 528/18 |
| 4,748,166 | 5/1988 | Gautier et al. | 528/17 |
| 4,965,333 | 10/1990 | Inouye et al. | 528/17 |
| 4,973,644 | 11/1990 | Onishi et al. | 528/17 |
| 5,011,410 | 4/1991 | Culler et al. | 433/218 |
| 5,068,301 | 11/1991 | Okamura et al. | 528/18 |
| 5,081,164 | 1/1992 | Lai | 526/279 |

FOREIGN PATENT DOCUMENTS

| | | |
|---|---|---|
| 0058514 | 2/1982 | European Pat. Off. . |
| 1222568 | 9/1968 | United Kingdom . |

OTHER PUBLICATIONS

W. Noll, *Chemie und Technologie der Silikone*, Verlag Chemie, 1968, whole text.

*Primary Examiner*—Paul R. Michl
*Assistant Examiner*—Andrew E. C. Merriam
*Attorney, Agent, or Firm*—Sprung Horn Kramer & Woods

[57] ABSTRACT

It has been found that silicone resins which contain alkoxy functional groups and harden rapidly in the presence of moisture allow suitable one-component formulations as provisional fixing materials. The hardening rate can be adjusted by addition of suitable activators.

7 Claims, No Drawings

PROVISIONAL LUTING MATERIALS

This is a division of application Ser. No. 07/858,912, filed on Mar. 27, 1992, now abandoned.

Provisional luting materials are often used in dental practice, for example for setting provisional crowns and bridges so that the patient is cared for over the period which the dental technician requires to produce the final dental prosthesis. However, definitive crowns and bridges are also often worn for a certain trial period in order to check the functional capacity before final incorporation. The crowns and bridges are also set with provisional cements in these cases. To be suitable as a provisional luting cement, the material must withstand the chewing pressure stresses throughout the entire wearing time, but on the other hand must be easily removed. It must be insoluble in saliva and seal the dentine wound tightly, it should have no irritating action and the dentist should be able to process it without problems.

Zinc oxide-eugenol cements have chiefly been used to date for this indication. The dentist mixes a paste containing zinc oxide with a eugenol paste as required. The mixture hardens within about 2–3 minutes.

If the dentist does not dose the material correctly or homogenises the two pastes incompletely, the cement does not harden completely and is not of sufficient strength. A larger or smaller residue moreover remains on the mixing block, which must be discarded after hardening.

The use of preparations containing eugenol is not harmless from the toxicological point of view and is contraindicated in some patients because of allergic reactions. The smell and taste of eugenol is furthermore often found to be unpleasant.

If a composite luting cement is used for subsequent final setting of the dental prosthesis, residues of the zinc oxide-eugenol cement in dentine tubuli and on the dental prosthesis leads to inhibition of the polymerisation and hence to an inadequate strength. This problem is becoming more and more significant due to the increasing use of composite cements.

In addition to eugenol-containing preparations, cements containing calcium hydroxide are also used for temporary setting of crowns and bridges.

As well as having the abovementioned problems of processing of two pastes and interaction with composite luting cements, these also display an inadequate mechanical strength and can therefore be used only for short-term provisional measures. In addition, a "mixing" operation is necessary with two-component materials in all cases.

It has now been found that silicone resins which contain alkoxy functional groups and harden rapidly in the presence of moisture allow suitable one-component formulations as provisional luting materials. The hardening rate can be adjusted by addition of suitable activators.

The mechanical strength can be modified within wide ranges, according to the intended requirement, by addition of fillers or plasticisers. The material can be coloured in the colour of teeth by customary pigments. The pastes have no smell or taste. The hardened material is inert and, for example, does not influence the hardening of composite cements. The materials according to the invention can be used without further working by the dentist. Mixing before use is omitted. The silicone resins according to the invention which contain alkoxy functional groups preferably correspond to the empirical formula

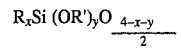

$$R_xSi(OR')_yO_{\frac{4-x-y}{2}}$$

in which

R denotes an alkyl or phenyl group,

R' denotes a methyl or ethyl group, x has a value of 0.75–1.75, preferably 0.95–1.5, and y has a value of 0.3–2.0, preferably 0.5–1.7.

However, the radicals R and R' can also represent different radicals having the abovementioned meaning, as explained in Example 6.

The following compositions may be mentioned as examples of pastes according to the invention:

| | |
|---|---|
| 15–98 parts by weight | of silicone resin containing alkoxy functional groups, preferably 15–40 parts by weight |
| 0–85 parts by weight | of fillers, preferably 20–70 parts by weight |
| 0–50 parts by weight | of plasticiser, preferably 2–20 parts by weight |
| 0.1–5 parts by weight | of activator, preferably 0.5–2 parts by weight |
| 0–1 part by weight | of pigments |

Suitable silicone resins are, for example: methylsilicone resins containing methoxy or ethoxy functional groups, phenylsilicone resins containing methoxy or ethoxy functional groups, and mixtures thereof.

The silicone resins preferably have a molecular weight of 300 to 30,000, particularly preferably 800 to 10,000, especially preferably 1000 to 6200.

Such resins and their preparation are described in W. Noll: Chemie und Technologie der Silikone (Chemistry and Technology of the Silicones), Verlag Chemie, 1968.

Luting materials according to the invention preferably contain 15–40% by weight of the silicone resins containing alkoxy functional groups.

Suitable fillers are, for example: highly dispersed silicic acids, metal oxides, such as zinc oxide, magnesium oxide or aluminium oxide, calcium carbonate, calcium fluoride, glass powder or quartz powder and mixtures of these fillers. If appropriate, the fillers can be surface treated. The treatment is preferably carried out with silanes in the case of materials containing $SiO_2$ and is preferably carried out with long-chain carboxylic acids, such as stearic acid, in the case of basic substances such as $CaCO_3$ or ZnO. The fillers are preferably employed in the still dried form with residual water contents of <0.5% by weight. Powders of plastics, such as, for example, poly(meth)acrylate powder, can also be employed as fillers. The fillers preferably have an average particle size of <25 μm, preferably <15 μm, especially preferably <5 μm.

Suitable plasticisers are, for example, oligo- or polyethers and/or polyether-polysiloxane compounds and/or hydrocarbon compounds which are soluble in silicone resin, such as, for example: silicone oils, polyether-polysiloxanes, phenolalkylsulphonic acid esters, polyethylene glycol ethers or esters, dibenzyltoluene, paraffins and isoparaffins (for example isoeicosane) and mixtures of these compounds.

Suitable activators are, for example: organic tin, zirconium or titanium compounds, such as dibutyltin dilaurate, tin(II) octoate, titanium tetrabutylate, tetrapropyl titanate, tetraethyl titanate, corresponding alkyl zirconates or mixtures of these activators.

The following examples serve to illustrate the invention:

Example 1

| | |
|---|---|
| 26 | parts by weight of methylsilicone resin containing methoxy functional groups* |
| 38 | parts by weight of zinc white |
| 12 | parts by weight of hydrophobised highly disperse silicic acid |
| 21.5 | parts by weight of isoeicosane |
| 2.5 | parts by weight of tetrapropyl titanate | are processed to a paste with exclusion of moisture.

empirical formula: $MeSi(OMe)_{0.88}(O)_{\frac{2.12}{2}}$
(by NMR spectroscopy; Me = methyl)
Viscosity: 40.2 mPas
Density: 1.150 g/ml The paste is introduced into the object to be fixed (crown or bridge) and positioned on the prepared tooth stump. After 2 minutes, the excess material can be removed. If required, the objects can be removed again without effort and the hardened brittle material can be broken off with a dental probe.

Example 2

| | |
|---|---|
| 23 | parts by weight of methylsilicone resin containing methoxy functional groups (from Example 1) |
| 30 | parts by weight of calcium fluoride |
| 25 | parts by weight of hydrophobised precipitated silicic acid |
| 19 | parts by weight of isoeicosane |
| 2.5 | parts by weight of tetrabutyl titanate |
| 0.5 | part by weight of pigments | are processed to a paste with exclusion of moisture.

Hardening of the cement takes 3 minutes (skin formation at 36° C. and 95% relative humidity). The material has a compressive strength of 15 MPa after 24 hours.

Example 3

| | |
|---|---|
| 50 | parts by weight of methylsilicone resin containing methoxy functional groups (from Example 1) |
| 50 | parts by weight of surface treated chalk | are processed to a paste with exclusion of moisture.

Various amounts of activator are added to the pastes and the hardening time (skin formation at 36° C. and 95% relative humidity) and compressive strength (after 24 hours at 23° C. and 95% relative humidity) are measured.

| Activator content (parts by weight, based on the silicone resin) | Hardening time | Compressive strength (MPa) |
|---|---|---|
| 0.5 of dibutyltin dilaurate | | |
| 0.5 of tetrabutyl titanate | 2' | 20 |
| 1 of dibutyltin dilaurate | 7' | 35 |
| 10 of tetrabutyl titanate | 4'30" | 25 |
| 10 of tetrabutyl zirconate | 5'30" | 30 |

Example 4

Various proportions of filler are incorporated into a solution of 5% by weight of tetrabutyl titanate in a silicone resin containing methoxy functional groups (from Example 1) with exclusion of moisture and the hardening time (skin formation at 36° C. and 95% relative humidity) and compressive strength (after 24 hours at 23° C. and 95% relative humidity) are measured.

| Filler | Hardening time | Compressive strength (MPa) |
|---|---|---|
| 50 parts by weight of solution + 50 parts by weight of chalk | 6' | 25 |
| 67 parts by weight of solution + 33 parts by weight of precipitated silicic acid | 3'3" | 30 |
| 90 parts by weight of solution + 10 parts by weight of acrylic ester polymer | 2'30" | 17 |

Example 5

A solution of 5% by weight of tetrabutyl orthotitanate in methylsilicone resin containing methoxy functional groups (from Example 1) is processed to a paste with equal parts of surface treated chalk. Various proportions of plasticiser are added to this paste and the hardening time (skin formation at 36° C. and 95% relative humidity) and compressive strength (after 24 hours at 23° C. and 95% relative humidity) are measured.

| Diluent | Hardening time | Compressive strength (MPa) |
|---|---|---|
| 7.5 parts by weight of triethylene glycol triacetate | 6' | 11.5 |
| 7 parts by weight of polyoxalkylated polysiloxane | 14" | 12 |

Example 6

| | |
|---|---|
| 49.5 | parts by weight of silicone resin |
| 49.5 | parts by weight of surface treated chalk |
| 0.5 | part by weight of dibutyltin dilaurate |
| 0.5 | part by weight of tetrabutyl titanate | are processed to a paste with exclusion of moisture and the hardening time (skin formation at 60% relative humidity and 23° C.) is measured.

| Silicone resin | Hardening time (minutes) | Empirical formula |
|---|---|---|
| Methylsilicone resin containing methoxy functional groups | 4' | $(Me)_{1.0}Si(OMe)_{0.88}(O)_{\frac{2.12}{2}}$ |

| Silicone resin | Hardening time (minutes) | Empirical formula |
|---|---|---|
| Methyl-phenyl-silicone resin containing methoxy functional groups | 7' | $(Me)_{0.8}(Ph)_{0.7}Si(OMe)_{0.44}O_{\frac{2.06}{2}}$ |
| Methyl-phenyl-silicone resin containing ethoxy functional groups | 7' | $(Me)_{0.4}(Ph)_{0.8}Si(OEt)_{0.95}O_{\frac{1.84}{2}}$ |
| Methyl-phenyl-silicone resin containing ethoxy functional groups | 45' | $(Me)_{0.7}(Ph)_{0.3}Si(OMe)_{0.84}O_{\frac{2.16}{2}}$ |

We claim:

1. A method of provisionally securing a provisional dental prosthesis to teeth by applying therebetween a water-free luting material which includes a silicone resin which contains alkoxy functional groups and has the empirical formula $$R_xSi(OR')_yO_{\frac{4-x-y}{2}}$$

wherein
R is an alkyl or phenyl group,
R' is a methyl or ethyl group,
x has a value of 0.75–1.75 and
y has a value of 0.3–2.0.
and further includes an activator, and letting said luting material harden thereby temporarily to bond said prosthesis to said teeth.

2. The method according to claim 1, wherein said luting material consists essentially of a single component by weight consisting essentially of

| | |
|---|---|
| 15–98 | parts by weight of silicone resin containing alkoxy functional groups |
| 0–85 | parts by weight of filler |
| 0–50 | parts by weight of plasticiser |
| 0.1–5 | parts by weight of activator |
| 0–1 | parts by weight of pigments, | the luting material hardening in the oral cavity in from 2 to 14 minutes to a brittle resin having a compressive strength of 11.5 to 30 MPa.

3. The method according to claim 1, wherein the activator is a titanium, zirconium or tin compound.

4. The method according to claim 2, wherein the plasticizer is at least one of an oligo- or polyether, a polyetherpolysiloxane compound and a hydrocarbon compound which is soluble in the silicone resin.

5. The method according to claim 2, wherein the luting material contains 15 to 40 parts by weight of the silicone resin.

6. The method according to claim 2, wherein the activator is a titanium, zirconium or tin compound, the plasticizer is at least one of an oligo- or polyether, a polyetherpolysiloxane compound and a hydrocarbon compound which is soluble in the silicone resin, the silicone resin is present in from 15 to 40 parts by weight, and the prosthesis comprises a crown or bridge.

7. The method according to claim 2, wherein the luting material contains at least 2 parts by weight of plasticizer.

* * * * *

UNITED STATES PATENT AND TRADEMARK OFFICE
CERTIFICATE OF CORRECTION

PATENT NO. : 5,548,002
DATED : August 20, 1996
INVENTOR(S) : Schwabe, et al.

It is certified that error appears in the above-indentified patent and that said Letters Patent is hereby corrected as shown below:

Title Page    Insert -- [30] Foreign Application Priority
              Data:  Apr. 4, 1991 [DE] Germany......
              41 10 796.9 --

Signed and Sealed this

Twenty-fifth Day of February, 1997

Attest:

BRUCE LEHMAN

*Attesting Officer*     *Commissioner of Patents and Trademarks*